(12) United States Patent
Lindgren

(10) Patent No.: US 6,952,609 B1
(45) Date of Patent: Oct. 4, 2005

(54) CARDIAC STIMULATING DEVICE

(75) Inventor: Anders Lindgren, Täby (SE)

(73) Assignee: St. Jude Medical AB, Jarfalla (SE)

( * ) Notice: Subject to any disclaimer, the term of this patent is extended or adjusted under 35 U.S.C. 154(b) by 325 days.

(21) Appl. No.: 10/130,878

(22) PCT Filed: Oct. 3, 2000

(86) PCT No.: PCT/SE00/01915

§ 371 (c)(1),
(2), (4) Date: May 22, 2002

(87) PCT Pub. No.: WO01/37928

PCT Pub. Date: May 31, 2001

(30) Foreign Application Priority Data

Nov. 22, 1999 (SE) .................................. 9904227

(51) Int. Cl.[7] ............................................ A61N 1/362
(52) U.S. Cl. .............................. 607/9; 607/15; 607/17
(58) Field of Search ..................... 607/9, 11, 14, 16–17, 607/25–27

(56) References Cited

U.S. PATENT DOCUMENTS

| | | | |
|---|---|---|---|
| 5,476,487 A | 12/1995 | Sholder | 607/28 |
| 5,741,312 A * | 4/1998 | Vonk et al. | 607/28 |
| 5,873,895 A | 2/1999 | Sholder et al. | 607/9 |
| 5,928,271 A | 7/1999 | Hess et al. | 607/14 |
| 6,148,234 A * | 11/2000 | Struble | 607/28 |
| 6,311,089 B1 * | 10/2001 | Mann et al. | 607/30 |

FOREIGN PATENT DOCUMENTS

EP    0 770 408    10/1996    .......... A61N 1/368

* cited by examiner

*Primary Examiner*—Carl Layno
(74) *Attorney, Agent, or Firm*—Schiff Hardin LLP

(57) ABSTRACT

An implantable cardiac stimulating device has an atrial pulse generator and an atrial sensor connected to an atrial electrode, for delivering stimulating pulses to the atrium and sensing events in the atrium. The stimulating device also has a ventricular pulse generator and a ventricular sensor connected to a ventricular electrode for delivering stimulating pulses to the ventricle and for sensing events in the ventricle. The ventricular sensor also includes an evoked response detector. A control unit causes the ventricular pulse generator to deliver a back-up pulse if no evoked response is detected. The control unit operates the atrial pulse generator in a first manner wherein no stimulating pulse is delivered to the atrium and in a second manner wherein stimulating pulses are delivered to the atrium. The control unit prevents delivery of the back-up pulse at least during a first heart cycle following a time at which the control unit changes from the first manner of operation of the atrial pulse generator to the second manner of operation.

7 Claims, 2 Drawing Sheets

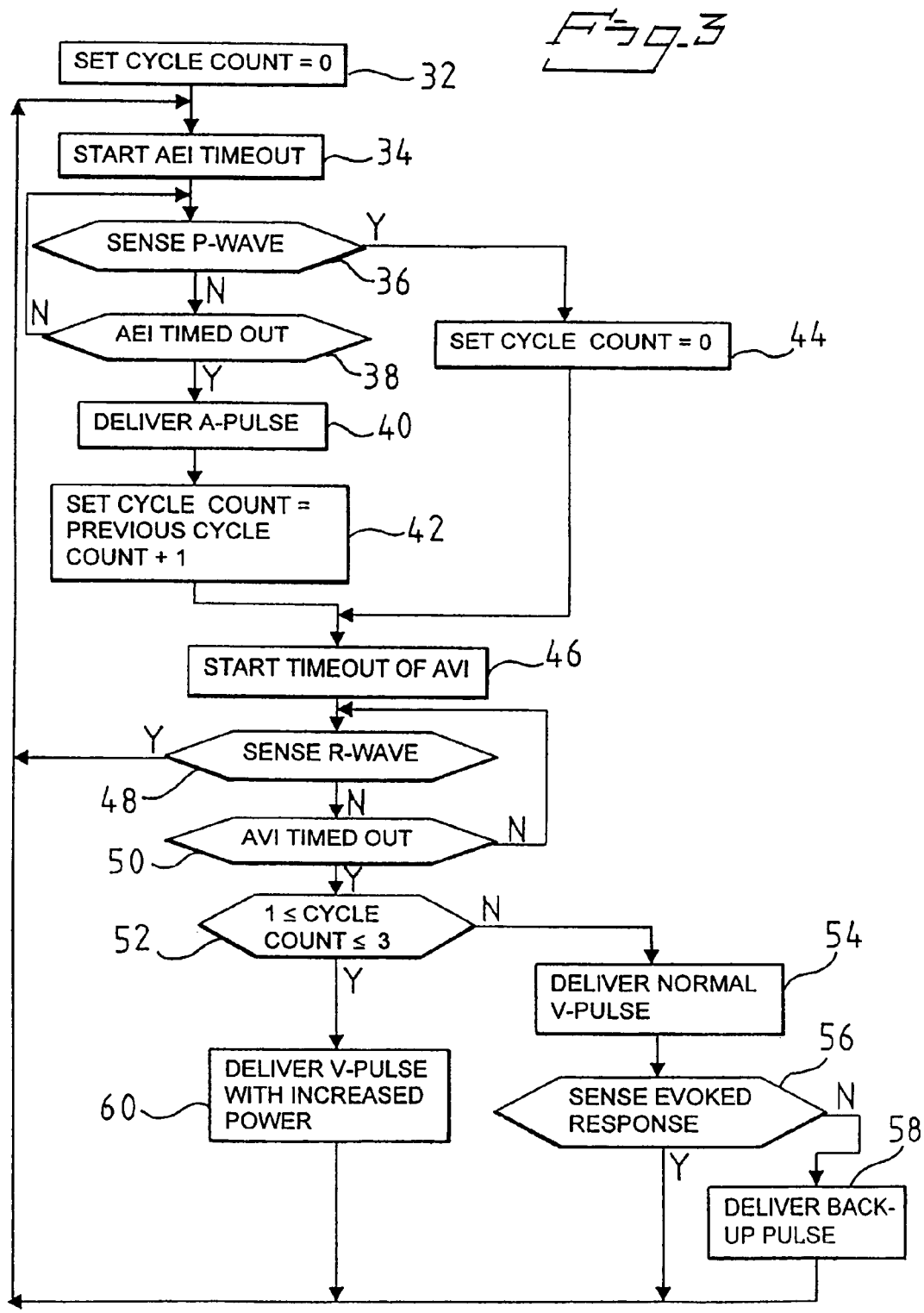

CARDIAC STIMULATING DEVICE

BACKGROUND OF THE INVENTION

1. Field of the Invention

The present invention relates to an implantable cardiac stimulating device.

More precisely, the invention concerns a dual chamber pacemaker, i.e. a pacemaker which is adapted to stimulate and/or sense both an atrium and a ventricle of the heart. In particular, the invention concerns a, pacemaker which includes means to deliver stimulating pulses to the atrium and to the ventricle and means for sensing events in the atrium and in the ventricle. The means arranged for sensing events in the ventricle includes means for sensing an evoked response of the ventricle to a delivered stimulating pulse. Furthermore, the cardiac stimulating device includes means which may be arranged to deliver a back-up pulse to the ventricle if the means arranged to sense an evoked response does not sense any evoked response to a delivered stimulating pulse. Moreover, the cardiac stimulating device includes a control system which is arranged to operate the device in at least a first and a second manner, wherein according to the first manner no stimulating pulse is delivered to the atrium and according to the second manner, stimulating pulses are delivered to the atrium. Such a control system may work in response to the means for sensing events in the atrium, such that a pulse is delivered to the atrium if and only if no event is sensed in the atrium within the atrial escape interval.

2. Description of the Prior Art

For a general overview of the function of an implantable cardiac stimulating device, see, for example, U.S. Pat. No. 5,873,895, columns 2–5.

U.S. Pat. No. 5,476,487 describes the function of an implantable cardiac stimulating device which emits a back-up pulse to the ventricle when no evoked response is detected to an applied ventricular pulse; see in particular columns 1–2.

A cardiac stimulating device which operates with such back-up pulses is hereinafter also called an autocapture pacemaker (Autocapture™ pacing system). Such a pacemaker may operate in the following manner. Shortly after a ventricular pulse has been delivered, for example 5–20 ms after the delivery, the pacemaker begins sensing whether a response occurs in the ventricle. This sensing may, for example, take place during 40–60 ms. If a response is sensed during this time interval, then no back-up pulse is emitted. However, if no evoked response is sensed, then a back-up pulse is emitted. The back-up pulse is preferably emitted immediately at the elapse of this time interval. The back-up pulse is usually emitted with increased output power in order to secure capture of the heart. For example, the normal ventricular pulse may be emitted with an amplitude of 1.5 V and the back-up pulses may be emitted with an amplitude of 4.5V.

In order to facilitate the understanding of the present invention, some basic working principles of a normal dual chamber pacemaker according to the prior art will now be described with reference to FIG. 1. FIG. 1 schematically depicts a timing/waveform diagram indicating cardiac and pacemaker events. A represents a stimulating pulse delivered to the atrium. V represents a stimulating pulse delivered to the ventricle. P indicates the atrial depolarization, in this case a paced depolarization. R indicates ventricular depolarization. R is thus in this case the evoked response to a delivered ventricular pulse V. T represents the ventricular repolarization. A heart cycle HC, as this concept is used in the present description and in the following claims, starts with a paced or sensed atrial event and ends at the subsequent paced or sensed atrial event.

AVI is the so-called AV-interval. This is a pre-set, normally programmable, time interval beginning with a sensed or paced atrial event. If no ventricular event is sensed during the AV-interval, then a ventricular pulse is delivered at the end of this interval. A normal AV-interval may have a length of, for example, 150–210 ms. AEI indicates the atrial escape interval. This is a predetermined, normally programmable, time interval which starts with an atrial or a ventricular sensed or paced event. If no atrial event has been sensed at the end of this pre-set atrial escape interval, then a stimulating pulse is delivered to the atrium at the end of this interval. BP is the ventricular blanking period. This is a short time interval after the delivery of an atrial pulse during which interval the ventricular sense amplifier is disabled and therefore cannot detect any signals. If there were no ventricular blanking period, then the ventricular sense amplifier could sense a paced event in the atrium and interpret this as a ventricular event. The pacemaker normally also operates with a similar atrial blanking period (which is not shown in FIG. 1).

Additionally, the following concepts, which are not shown in FIG. 1, will be explained. The "ventricular biological refractory period" is a period following a ventricular event (an R-wave) during which the heart will not respond to a ventricular stimulation. The "vulnerable period" is a part of the heart cycle, normally coincident with a part of the T-wave, during which a stimulation pulse may possibly cause repetitive rhythms such as, for example, tachycardia or ventricular fibrillation. The "ventricular complex" includes the ventricular depolarization and a short time before and after this depolarization.

The above explanations of the aforementioned concepts are not intended as absolute definitions, but rather as examples of how these concepts are normally used. Furthermore, it should be noted that in FIG. 1 no back-up pulses are shown. The function of an autocapture pacemaker will thus involve additional time intervals, as described above in connection with the explanation of the function of a pacemaker working with back-up pulses.

SUMMARY OF THE INVENTION

Although the above-described dual chamber pacemakers, which also emit back-up pulses, have been found to function well, the inventor of the present invention has invented further improvements concerning such pacemakers.

In particular, the inventor has found that in such pacemakers a stimulating back-up pulse to the ventricle may sometimes occur during a phase of the heart cycle when such a stimulating pulse is not wanted. It has been found that such unwanted pulses may be initiated for example after the occurrence of a PVC (PVC=Premature Ventricular Contraction, i.e. a ventricular complex which occurs early) or in case an actual atrial event is not sensed by the pacemaker. Furthermore, the inventor has found that such an unwanted pulse is more likely to occur when the pacemaker changes its manner of operation from a period in which no stimulating pulse has been delivered to the atrium to a period in which one or more stimulating pulses are delivered to the atrium. The inventor has found that such a situation may occur in connection with, inter alia, the following circumstances: when a normal sinus node activity is not sensed (undersensing); in case of an ectopic focus (for example when the AV-node is the stimulating source); in case of atrial flutter or fibrillation; in case of atrial noise mode operation of the pacemaker; in case a sensor operated pacemaker (i.e. a pacemaker in which the stimulation rate changes with physical activity) changes the pacing rate.

As an example of a series of events which may lead to an unwanted back-up pulse, the inventor has found that the following may happen. An atrial stimulating pulse may sometimes in fact be delivered just before or during a following ventricular complex. This may for example happen if there is a premature ventricular contraction or if an atrial event which occurs is not sensed by the pacemaker. After an atrial stimulating pulse is delivered by the pacemaker, this pulse is followed by the above-mentioned ventricular blanking period. Since no event can be detected in the ventricle during this blanking period, the pacemaker will not sense a spontaneous ventricular depolarization and will therefore emit a ventricular pulse at the end of the AV-interval. This ventricular pulse may occur during the ventricular biological refractory period. Therefore, this pulse will not initiate a ventricular depolarization. Since no depolarization is sensed in response to the delivered pulse, the pacemaker will deliver a back-up pulse in accordance with the autocapture function. Since in this case a ventricular event has in fact occurred, this back-up pulse is not needed. Furthermore, this back-up pulse may be emitted during the above-mentioned vulnerable phase of the heart cycle.

An object of the present invention is to obtain an improved dual chamber autocapture pacemaker. A further object is to avoid the delivery of unnecessary back-up pulses at a point in time at which such pulses are not wanted. In particular, the invention aims at avoiding the delivery of such unwanted back-up pulses when the pacemaker changes its manner of operation to a manner in which one or more atrial pulses are delivered.

The above objects are achieved in accordance with the principles of the present invention in an implantable cardiac stimulating device connected to a first electrode adapted to be positioned to stimulate and sense an atrium and to a second electrode adapted to stimulate and sense a ventricle, a pulse generator which delivers stimulating pulses via said first electrode to the atrium, a sensor connected to said first electrode for sensing events in the atrium, a pulse generator connected to the second electrode to deliver stimulating pulses to the ventricle, a sensor connected to the second electrode for sensing events in the ventricle, the ventricular sensor including an evoked response detector for detecting an evoked response of the ventricle to a delivered stimulating pulse to the ventricle, the ventricular pulse generator delivering a back-up pulse to the ventricle if the evoked response detector does not sense any evoked response to a delivered stimulating pulse, a control unit for controlling at least said atrial pulse generator dependent on said atrial sensor, in a first manner wherein no stimulating pulse is delivered to the atrium and in a second manner wherein stimulating pulses are delivered to the atrium, and said control unit preventing delivery of the back-up pulses to the ventricle during at least a first heart cycle from a point in time when said control unit changes from said first manner of operation to said second manner of operation.

Since no back-up pulse is delivered during the first heart cycle, the above mentioned occurrence of an unwanted back-up pulse is avoided during, at least, the heart cycle when the pacemaker changes from the first to the second manner of operation.

According to a preferred embodiment of the invention, the control system prevents the delivery of the back-up pulses during a predetermined number of consecutive heart cycles starting with the first heart cycle, the predetermined number being larger than 1. It has been found to be beneficial to prevent the delivery of back-up pulses during a number of heart cycles after said change in the manner of operation.

According to a further embodiment of the invention, this predetermined number is 2–5, preferably 2 or 3. It has been found to be advantageous to limit the number of consecutive heart cycles during which no back-up pulses are delivered. The probability of unwanted back-up pulses has been found to be higher during the first heart cycles after said change in the manner of operation. Furthermore, it is beneficial to allow the delivery of back-up pulses after the elapse of some heart cycles, since such back-up pulses, during normal operation, aid in securing the capture of the heart. The inventor has found that to prevent the delivery of the back-up pulses during the first two or three heart cycles after said change in the manner operation is particularly beneficial.

According to a further embodiment of the invention, the ventricular pulse delivery unit delivers the stimulating pulses to the ventricle with increased output power during the heart cycles in which the control system prevents the delivery of the back-up pulses. Since the output power of the stimulating pulses is increased, the likelihood that the heart actually will respond to the delivered stimulating pulses increases.

According to a further embodiment of the invention, this increased output power is of essentially the same magnitude as that at which the back-up pulses are delivered.

DESCRIPTION OF THE DRAWINGS

FIG. 3 is a simplified flow chart illustrating an example of the operation of the implantable cardiac stimulating device according to the invention.

DESCRIPTION OF THE PREFERRED EMBODIMENTS

Figure 1:
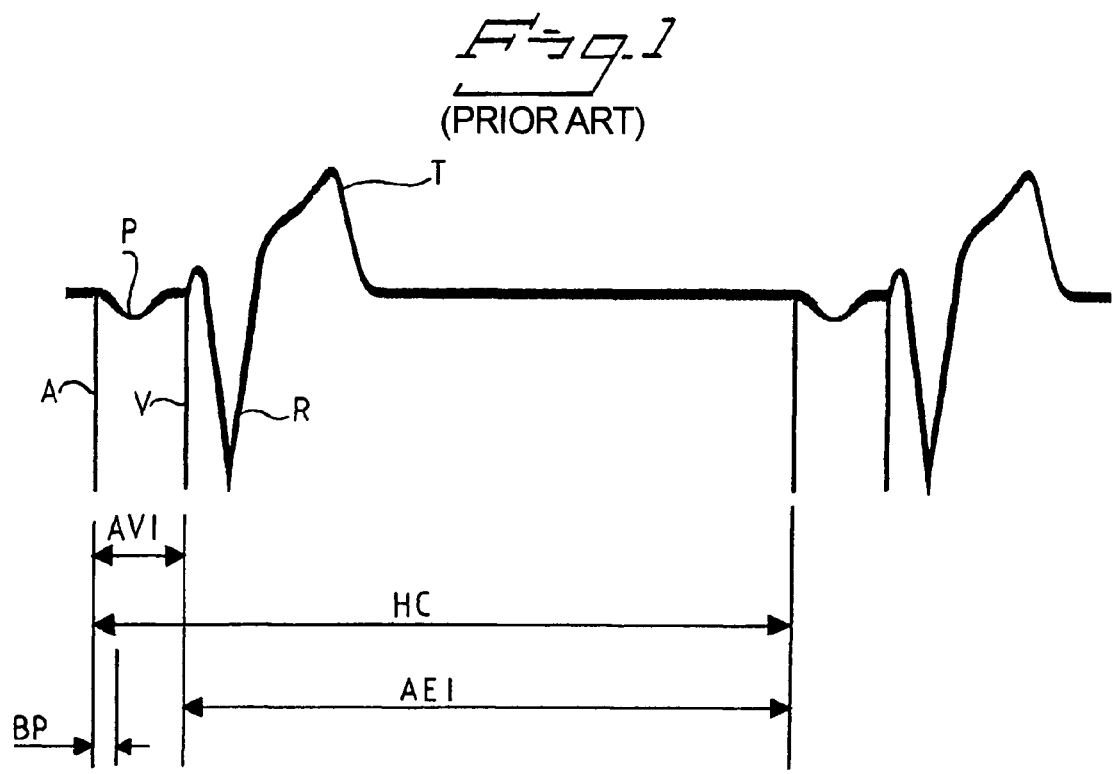
FIG. 1 is a timing/waveform diagram depicting cardiac pacemaker events in a conventional dual chamber implantable cardiac stimulating device.
Figure 2:
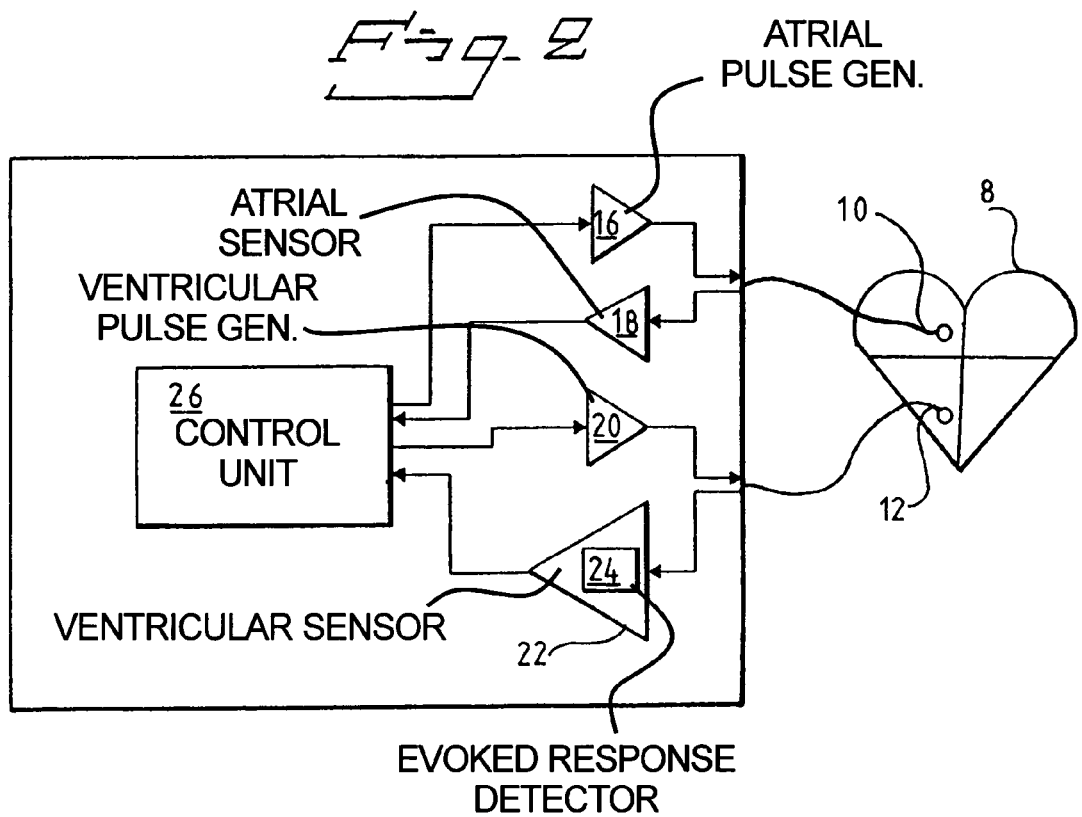
FIG. 2 is a schematic block diagram of a cardiac stimulating device constructed and operating in accordance with the principles of the present invention.

FIG. 2 schematically shows an implantable cardiac stimulating device according to the present invention. The implantable cardiac stimulating device is hereinafter also called a pacemaker. The invention concerns dual chamber pacemakers. The pacemaker is thus adapted to be connected to a first electrode 10 to be positioned to stimulate and sense an atrium of the heart. The heart is schematically depicted by 8. The pacemaker is also adapted to be connected to a second electrode 12 to be positioned to stimulate and sense a ventricle of the heart.

The pacemaker also includes a pulse-generating arrangement for producing stimulating pulses. In particular the pacemaker includes an atrial pulse generator 16 arranged to deliver stimulating pulses to the atrium and an atrial sensor 18 arranged for sensing events in the atrium. Furthermore, it includes a ventricular pulse generator 20 arranged to deliver stimulating pulses to the ventricle and a sensor 22 arranged for sensing events in the ventricle. The sensor 22 arranged for sensing events in the ventricle includes an evoked response detector 24 arranged to sense an evoked response of the ventricle to a delivered stimulating pulse. The evoked response detector 24 may function as described above, i.e. to sense the evoked response during a certain time interval after the delivery of a stimulating pulse.

The ventricular pulse generator 20, during normal operation conditions, delivers a backup pulse to the ventricle if the evoked response detector 24 does not sense any evoked response to a delivered stimulating pulse.

The pacemaker also includes a control system 26 arranged to automatically control the operation of the pacemaker. In particular, the control system 26 causes a stimulating pulse to be delivered to the atrium if no relevant event has been sensed in the atrium during a predetermined period of time. It can thus be said that the control system 26 operates the pacemaker in a first manner and a second manner, wherein in the first manner no stimulating pulse is delivered to the atrium and in the second manner stimulating pulses are delivered to the atrium. According to the second manner of operation a stimulating pulse thus is delivered to the atrium upon the elapse of a predetermined time interval, for example at the elapse of the atrial escape interval. Furthermore, according to the present invention, the control system 26 causes no back-up pulse to be delivered to the ventricle during at least the first heart cycle from the point in time when the pacemaker starts an episode of operating in the second manner.

Preferably, the delivery of back-up pulses is prevented during a predetermined number of consecutive heart cycles starting from said point in time. This predetermined number of heart cycles may for example be 1–9, preferably 2–5, in particular 2 or 3. During these heart cycles, the pacemaker may be arranged to deliver the ventricular stimulating pulses with an increased output power. The ventricular pulses may normally for example have an amplitude of between 1 and 2 V. The amplitude of the ventricular pulses with increased output power may be, for example, between 4 and 5 V. The ventricular pulses may thereby be delivered at a maximum output power, which may substantially correspond to the output power at which the back-up pulses are normally delivered.

It should be noted that it may, of course, happen that an episode of pacing in the second manner only comprises one heart cycle. In this case it is sufficient to prevent the delivery of the back-up pulse during this heart cycle. It is, however, also possible to arrange the control system 26 such that back-up pulses are prevented during a predetermined number of heart cycles (e.g. 3) even if the episode of pacing according to the second manner only comprises one (or two) heart cycles. As an alternative to counting the number of heart cycles, the control system 26 can be arranged such that the pacemaker goes back to the normal operation (i.e. with back-up pulses) after a predetermined time. However, independently of in which way the pacemaker is arranged in order to inhibit the back-up pulses, it is preferred that a possible back-up pulse is inhibited for at least one heart cycle as soon as a pacing pulse is delivered to the atrium in the case when no pacing pulse was delivered to the atrium during the preceding heart cycle.

FIG. 3 shows a simplified flow chart of the operation of the pacemaker according to the invention. In FIG. 3 Y stands for yes and N for no. At 32, a cycle count is set to 0. The purpose of the cycle count is to count the number of consecutive heart cycles during which a stimulating pulse is delivered to the atrium. At 34, the timer counting the atrial escape interval is started. If no P-wave is sensed during the atrial escape interval (blocks 36 and 38), then a stimulating pulse is delivered to the atrium (block 40). Furthermore, the cycle count is increased by 1 (block 42). If a P-wave is sensed during the atrial escape interval, then the cycle count is set to be 0 (block 44).

At block 46, the timing of the AV-interval starts. If an R-wave is sensed during the AV-interval (blocks 48 and 50), then a new atrial escape interval starts according to block 34. However, if no R-wave is sensed during the AV-interval, then a new decision is taken at block 52. If the cycle count is either 0 or higher than 3, then a normal ventricular stimulating pulse is delivered at block 54. If an evoked response is sensed, then the process goes back to block 34 to start the timing of a new atrial escape interval. If no evoked response is sensed, then a back-up pulse is delivered according to block 58. After the delivery of this back-up pulse, the process goes back to block 34. If the cycle count in block 52 is equal to 1, 2 or 3, then a ventricular pulse with increased output power is delivered at the end of the AV-interval (block 60). After the delivery of this ventricular pulse, the process goes back to block 34. In this case, therefore, no back-up pulse will be delivered.

It should be pointed out that FIG. 3 depicts a very simplified example of the operation of the pacemaker according to the invention. Additional or alternative time counters may be used. Furthermore, the operation of the pacemaker normally involves several other parameters which are not indicated in the simplified flow charts, since the operation of a pacemaker is well known to the person skilled in the art. In FIG. 3 the critical number of heart cycles is set to be 3. This number is given only as an example, and the number of heart cycles can be set at other values as explained above.

Although modifications and changes may be suggested by those skilled in the art, it is the invention of the inventor to embody within the patent warranted heron all changes and modifications as reasonably and properly come within the scope of his contribution to the art.

I claim as my invention:

1. An implantable cardiac stimulating device adapted for use with a first electrode adapted to be positioned in an atrium of a heart and with a second electrode adapted to be positioned in a ventricle of the heart, said cardiac stimulating device comprising:

an atrial pulse generator adapted for connection to said first electrode for emitting atrial stimulating pulses;

an atrial sensor adapted for connection to said first electrode for sensing events in the atrium;

a ventricular pulse generator adapted for connection to said second electrode for emitting ventricular stimulating pulses;

a ventricular sensor adapted for connection to said second electrode for sensing events in the ventricle;

said ventricular sensor including an evoked response detector for detecting an evoked response of the ventricle to a ventricular stimulating pulse delivered to the ventricle;

said ventricular pulse generator delivering a back-up pulse to the ventricle if said evoked response detector does not detect any evoked response to a delivered ventricular stimulating pulse;

a control unit connected to said atrial pulse generator and to said ventricular pulse generator for, in response to events sensed in the atrium by said atrial sensor, operating said atrial pulse generator in a first manner wherein no atrial stimulating pulse is emitted, and operating said atrial pulse generator in a second manner wherein atrial stimulating pulses are generated; and said control unit operating said ventricular pulse generator to prevent delivery of said back-up pulse at least during a first heart cycle from a point in time when said control unit changes said atrial pulse generator from operation in said first manner to operation in said second manner.

2. An implantable cardiac stimulating device as claimed in claim 1 wherein said control unit prevents delivery of said back-up pulse during a predetermined number of consecutive heart cycles starting with said first heart cycle, said predetermined number being greater than 1.

3. An implantable cardiac stimulating device as claimed in claim 2 wherein said predetermined number is in a range 2–5.

4. An implantable cardiac stimulating device as claimed in claim 2 wherein said predetermined number is 2.

5. An implantable cardiac stimulating device as claimed in claim 2 wherein said predetermined number is 3.

6. An implantable cardiac stimulating device as claimed in claim 1 wherein said ventricular pulse generator emits said ventricular stimulating pulses with an increased output power during said at least one heart cycle in which said control unit prevents delivery of said back-up pulse.

7. An implantable cardiac stimulating device as claimed in claim 6 wherein said increased output power is of substantially a same magnitude as an output power of said back-up pulse.

* * * * *